United States Patent [19]

Steinberg

[11] Patent Number: 5,743,349
[45] Date of Patent: Apr. 28, 1998

[54] NON-INVASIVE OPTICAL BLOOD ALCOHOL CONCENTRATION READER AND VEHICLE IGNITION INTERLOCK SYSTEM AND METHOD

[76] Inventor: Steven Steinberg, 6851 Vista de Pueblo, Tucson, Ariz. 85750

[21] Appl. No.: 718,759

[22] Filed: Sep. 23, 1996

[51] Int. Cl.[6] .................................................. B60K 28/06
[52] U.S. Cl. ............................................................ 180/272
[58] Field of Search .............................................. 180/272

[56] References Cited

U.S. PATENT DOCUMENTS

| | | | |
|---|---|---|---|
| 3,831,707 | 8/1974 | Takeuchi | 280/272 |
| 3,855,573 | 12/1974 | Honda et al. | 280/272 |
| 4,723,625 | 2/1988 | Komlos | 280/272 |
| 4,738,333 | 4/1988 | Collier et al. | 180/272 |
| 4,809,810 | 3/1989 | Elfman et al. | 180/272 |
| 4,926,164 | 5/1990 | Porter et al. | 340/576 |
| 4,996,161 | 2/1991 | Conners et al. | 436/132 |
| 5,020,628 | 6/1991 | Bigliardi et al. | 180/272 |
| 5,224,566 | 7/1993 | Stepanian et al. | 280/272 |
| 5,348,003 | 9/1994 | Caro | 128/633 |
| 5,426,415 | 6/1995 | Prachar et al. | 340/576 |

OTHER PUBLICATIONS

Alcohol and the Human Body, "Intoximeter, Inc. 1995, (http://www.intox.com/Physiology.html) pp. 1–5 How Does a Pulse Oximeter Work" by NICL Laboratories, 1996, (http://www.nicl.com/labnotes/pulseox.html) pp. 1–2 User's Manual for the NELLCOR Pulse Oximeter (Model N–110C), Nellcor Inc. Hayward Ca. pp. 30–32.

*Primary Examiner*—Kenneth R. Rice
*Attorney, Agent, or Firm*—LaRiviere, Grubman & Payne

[57] ABSTRACT

A vehicle ignition interlock system including a non-invasive reader of a person's blood-alcohol concentration in combination with ignition interlock circuitry that prevents operation of a vehicle by an intoxicated person. The non-invasive blood-alcohol concentration reader, termed alcoh-meter, utilizes optical spectroscopic electromagnetic radiation technology to determine the alcohol levels in the blood. The alcoh-meter is preferably a dash mounted sensor for receiving a person's finger and absorbing incident light from a multiple wavelength light source and causing a light absorption reading to be generated based on the person's blood alcohol concentration in the finger tissue. After registering a reading, the results are compared electronically against a table of impaired/non-impaired levels of blood alcohol concentration. The impaired/non-impaired results are communicated to interlock circuitry that either enables, or disables start-up of the vehicle. If an impaired status is determined, the results are displayed instructing the operator to wait, or find a non-impaired operator.

18 Claims, 3 Drawing Sheets

NON-INVASIVE OPTICAL BLOOD ALCOHOL CONCENTRATION READER AND VEHICLE IGNITION INTERLOCK SYSTEM AND METHOD

FIELD OF THE INVENTION

The present invention relates to systems and methods for preventing the operation of a vehicle by an intoxicated person. More particularly, the present invention relates to electrical and electronic systems and methods for preventing the operation of a vehicle by an intoxicated person. Even more particularly, the present invention relates to electromagnetic radiation systems and methods for preventing the operation of a vehicle by an intoxicated person.

DESCRIPTION OF THE PRIOR ART

Alcohol denotes a family of organic chemicals that include ethanol, methanol isopropanol and others, ethanol being the type most commonly ingested and will be the typed referred to herein when using the term alcohol. Alcohol is a clear volatile liquid that is very soluble in water and is an organic compound consisting of carbon, oxygen and hydrogen. Alcohol is a central nervous system depressant, which system in a person's body is mostly affected by its consumption. The degree to which the person's central nervous system is impaired is directly proportional to the concentration of alcohol in the blood. When alcohol is ingested, it passes from the stomach into the small intestines, where it is rapidly absorbed into the blood and distributed throughout the body. The rapid distribution and high solubility of alcohol affects the central nervous system even in low concentrations. According to published information, the American Medical Association has defined the blood alcohol concentration (BAC) level of impairment for all people to be 0.04 grams/100 milliliters of blood (equivalent to 0.04 grams/210 liters of breath). Impairment including diminution of attention, judgment and control, beginning of sensory-motor impairment and loss of efficiency in finer performance tests. Further concentrations, for example, greater than 0.35 grams/100 milliliters of blood (equivalent to 0.35 grams/210 liters of breath) a person can become comatose and die. Additional information concerning the physical, chemical and physiological aspects of the consumption of alcohol can be found in an article entitled "Alcohol and the Human Body", Intoximeter, Inc. 1995, (http://www.intox.com/Physiology.html).

Technological advances have resulted in the invention of breath analyzer systems for gathering information about the blood alcohol concentration level of a person that has consumed alcohol. Exemplary of breath alcohol analyzer patents include U.S. Pat. Nos. 4,809,810 and 4,996,161. The '810 patent teaches comparing a reference BAC threshold to the breath sample from an individual, while the '161 patent teaches a system for breath alcohol testing of unsupervised individuals. The prior art also teaches systems that use blood alcohol testing systems in combination with systems for interlocking an automobile ignition to prevent operation of a vehicle when the operator is intoxicated. Exemplary of patents teaching interlocking a vehicle's ignition based on breath analyzer results include U.S. Pat. Nos. 4,738,333, 4,926,164, 5,020,628, and 5,426,415.

The use of breath analyzers in combination with interlock systems to prevent starting a vehicle by an intoxicated person is believed to have had limited success, perhaps because of the complexity and factors associated with the breath analyzer technology, such as time, temperature and other environmental conditions that can cause the output of the alcohol sensors to be inaccurate. Other technologies, aside from the breath analyzers, have not been considered to be combined with automobile interlock systems to prevent starting a vehicle by an intoxicated person. Advances in the medical field concerning blood analysis are believed to provide an insight to alternative technologies that can further commercial development of solutions to the problem of operation of vehicles by intoxicated drivers. For example, a medical device for analyzing blood, known as a pulse oximeter, measures the absorption of selected wavelengths of light passed a living tissue sample. Light transmitted through a living tissue site is partially absorbed by each constituent. The constituents include the skin, bone, venous blood, arterial blood and variable volume of arterial blood due to pulses from the heart. The pulsatile blood is of interest when using the pulse oximeter. The varying absorption of red and infrared light, as blood pulsates through a person's living tissue such, as a finger, is utilized by the oximeter to determine the percent of oxygen saturation of the person's blood. See generally an article entitled "How Does a Pulse Oximeter Work" by NICL Laboratories, 1996, (http://www.nicl.com/labnotes/pulseox.html), and a User's Manual for the NELLCOR Pulse Oximeter (Model N-110C), Nellcor Inc. Hayward, Calif. The possibility of extending the use of the non-invasive pulse oximeter type technology to measure blood alcohol concentration has been suggested in U.S. Pat. No. 5,348,003 (col. 17, lines 3–17). The optical spectroscopic technics known, although not to an absolute measurement accuracy as taught by U.S. Pat. No. 5,348,003, provide information about the optical absorption and hence about the chemical concentration of a particular species, in particular alcohol. However, there is no suggestion in the prior art to combine pulse oximeter technology, or other known optical spectroscopic electromagnetic radiation technology, including the technology taught by U.S. Pat. No. 5,348,003, with interlock circuitry to prevent operation of a vehicle by an intoxicated person.

Thus, a need is seen to exist for an automobile ignition interlock system that functions in combination with non-invasive optical spectroscopic electromagnetic radiation technology for preventing operation of a vehicle by an intoxicated person.

It is therefore a primary object of this invention to provide an automobile ignition interlock system that functions in combination with non-invasive optical spectroscopic electromagnetic radiation technology for preventing operation of a vehicle by an intoxicated person.

SUMMARY OF THE INVENTION

Accordingly, the foregoing objects are accomplished by providing a non-invasive reader of a person's blood-alcohol concentration, in combination with an ignition interlock circuitry that, in combination prevent operation of a vehicle by an intoxicated person. The non-invasive blood-alcohol concentration reader, herein termed alcoh-meter, utilizes optical spectroscopic electromagnetic radiation technology to determine the alcohol levels in the blood. Structurally, the alcoh-meter comprises a dash mounted sensor for receiving a person's finger, and which, in accordance with the invention, would respond with a reading indicative of the blood alcohol concentration level of the person. After registering a reading, the results are further compared electronically against a table of impaired/non-impaired levels of blood alcohol concentration. The impaired/non-impaired results are communicated to inter-lock circuitry that either enables, or disables start-up of the automobile. If an impaired status is determined, the results are displayed instructing the operator to wait, or find a non-impaired operator.

Therefore, to the accomplishments of the foregoing object, the invention consists of the foregoing features hereinafter fully described and particularly pointed out in the claims, the accompanying drawings and the following disclosure describing in detail the invention, such drawings and disclosure illustrating but one of the various ways in which the invention may be practiced.

DESCRIPTION OF THE PREFERRED EMBODIMENT OF THE INVENTION

Figure 1:
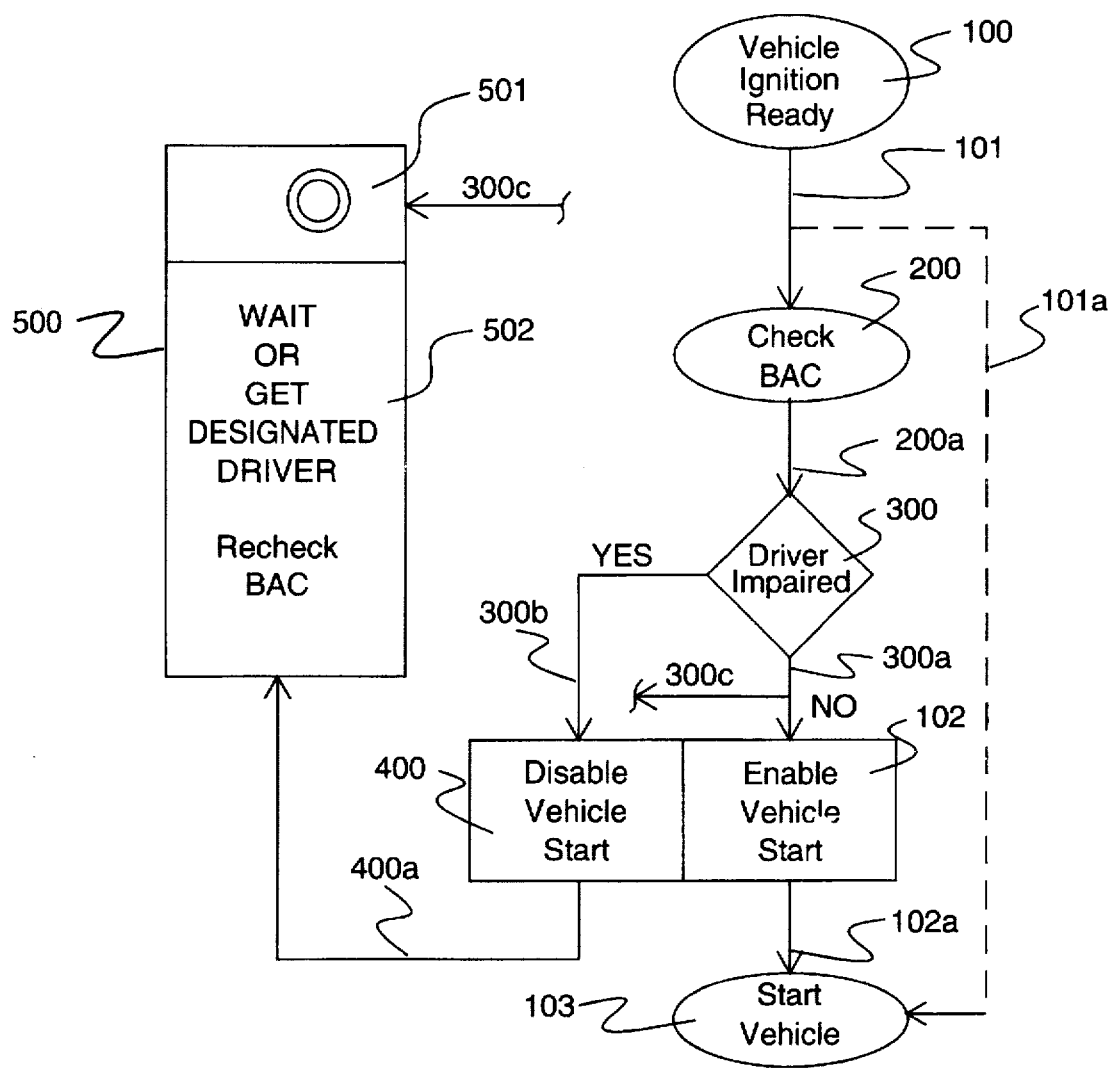
FIG. 1 is a block diagram representation of the blood-alcohol level reader and associated automobile ignition interlock system in accordance with the present invention.

FIG. 1 shows a vehicle ignition interlock system in accordance with the present invention comprising a vehicle's ignition circuitry 100 (see FIG. 3), a blood alcohol concentration reader (alcoh-meter) 200, electronic comparator circuitry 300, vehicle disable circuitry 400, and start-up status display circuitry 500. The vehicle's ignition is typically in a ready state for being actuated by an operator with a key to distribute electrical energy 101 throughout the vehicle's interlock system. As depicted in block diagram form in FIG. 1, and upon a vehicle's operator initiating a startup sequence, electrical energy 101 is supplied to alcoh-meter 200. Ordinarily, the electrical energy would comprise being supplied directly as electrical energy 101a to enable a start vehicle circuitry 103 without concern about the impairedness condition of the operator. However, the present invention functions without the connection for distributing energy 101a to start vehicle circuitry 103. The bypass connection may be effected, as illustrated, only under emergency condition by trained technicians. Accordingly, alcoh-meter 200 is energized upon turning the ignition on and is ready to receive, by example, an operator's right hand index finger. Alcoh-meter 200 utilizes electromagnetic radiation technology as a means for measuring the concentration of alcohol in the blood of the operator. Alcoh-meter 200 measures the attenuation of light, as it passes through an operator's index finger F in the form of a reading 200a, see FIG. 2. Reading 200a is then compared against stored blood-alcohol concentration data in electronic comparator circuitry 300. A first possible result generated during the comparison in comparator circuitry 300 is in the form of an electronic signal 300a indicating that reading 200a is below a predetermined non-impaired blood alcohol concentration threshold level, by example, a threshold level of less than 0.10 grams of blood per 100 milliliters. If the results is a 300a signal, then a non-impaired display signal 300c is also generated and sent to display panel 500 and associated visual indicator 501, by example a green light. Further, signal 300a is distributed to the coil of a normally open relay 102 which facilitates the distribution of power 102a to start vehicle circuitry 103. A second possible result generated during the comparison in comparator circuit 300 is an electronic signal 300b indicating an impaired operator whose blood alcohol reading is above, or at, a predetermined blood alcohol concentration level, by example, a threshold level greater than or equal to 0.10 grams of blood per 100 milli-liters. Signal 300b energizes normally open relay 400 and causes distribution of power signal 400a to display panel 500. At display panel 500, the operator is presented with a visual message at message screen 502 to recheck his or her blood alcohol concentration level, and or wait until sober, or get a designated driver whose blood alcohol level will pass the impairedness test for starting the vehicle.

Figure 2:
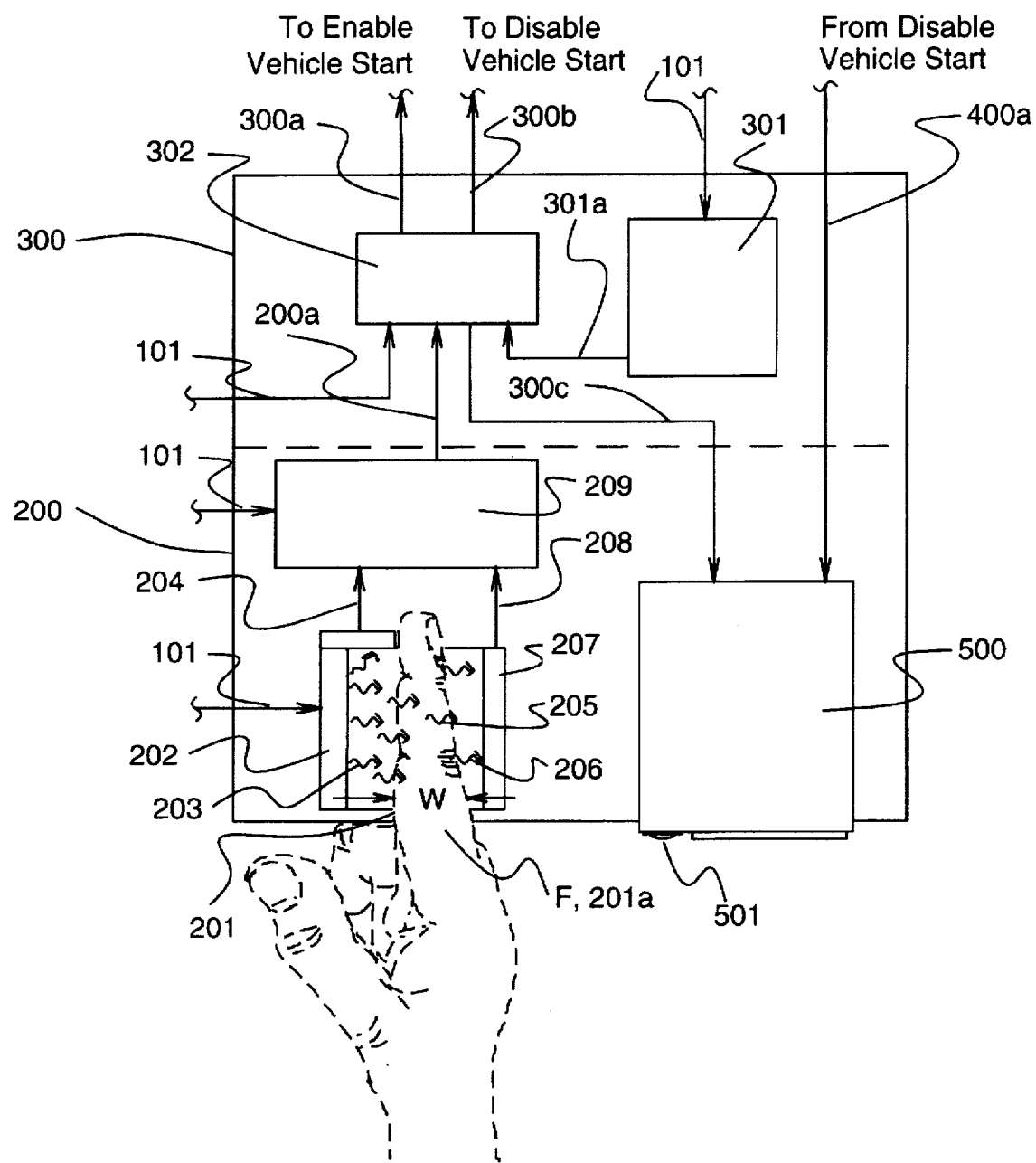
FIG. 2 shows a block diagram representation of the finger-type of non-invasive blood-alcohol level reader, associated impaired determining circuitry and system status display in accordance with the present invention.
Figure 3:
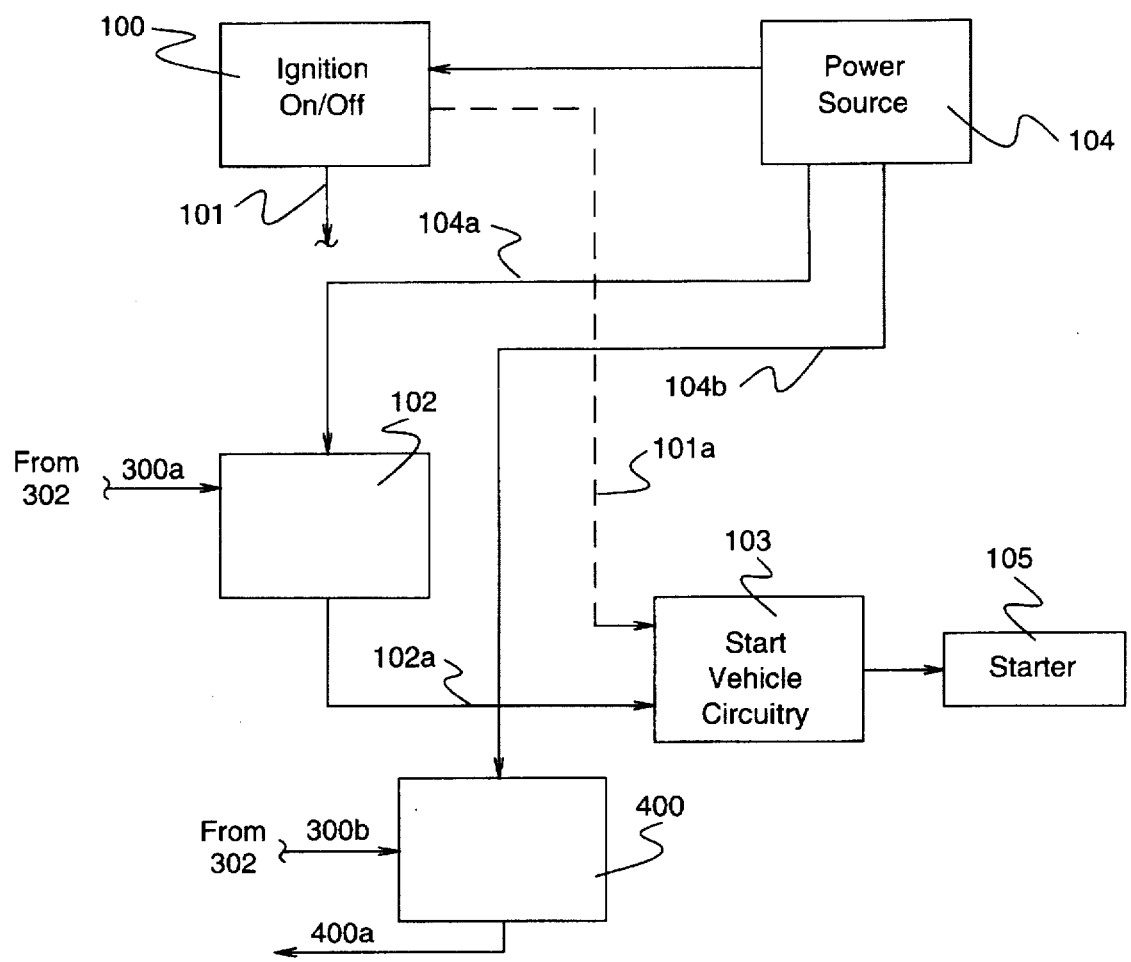
FIG. 3 shows a block diagram representation of the automobile interlock circuitry associated with preventing an alcohol impaired driver from starting an automobile in accordance with the present invention.

FIG. 2 further shows a block diagram representation of the finger-type alcoh-meter 200, the associated impaired determining circuitry 300 and system status display 500, in accordance with the present invention. As illustrated, alcoh-meter 200 comprises electrical energy 101 being distributed to a source of electromagnetic energy in the form of light source 202 for emitting multiple wavelengths (typically in the range in the range of 250 to 3000 nanometers) of light 203 for use in conducting the blood alcohol concentration test. Distribution of energy 101 to light source 202 is controlled on/off at entry port 201 by inserting finger F into enclosure 201a, or extracting finger F from within enclosure 201a. As illustrated, finger F is inserted into enclosure 201a and has caused light 203 to be recorded as recorded incident light 204 on the tissue, and to pass through the finger width, denoted generally as W, and be absorbed as absorbed light 205 and to emanate from the opposite side of the tissue as emanating light 206 which is collected in collector 207 as collected light 208. Collected light 208 is manipulated in analyzer and comparator 209 considering recorded incident light 204 data to determine light absorption information through finger F and to give a reading 200a representative of the operator's blood alcohol concentration level. Light absorption data and corresponding blood alcohol concentrations levels relative to a distance W, are contained and used in analyzer and comparator 209 to yield reading 200a. During analysis, a particularly determined light absorption quantity is matched against the contained light absorption data and corresponding blood alcohol concentrations levels in analyzer and comparator 209 to give reading 200a. Reading 200a is then compared against stored impairedness blood-alcohol concentration data in electronic comparator circuitry 300, in particular comparator 302. Comparator 302 receives a reference threshold blood alcohol concentration reading 301a representing an impaired threshold level from storage element 301. Comparator 302 generates a first possible result in the form of an electronic signal 300a indicating that reading 200a is below a predetermined non-impaired blood alcohol concentration threshold level, by example, a threshold level of less than 0.10 grams of blood per 100 milli-liters. Also, as discussed previously, if the results is a 300a signal, then a non-impaired display signal 300c is also generated and sent to display panel 500 and associated visual indicator 501, by example a green light. Further, and by referring to FIG. 3, signal 300a is distributed to the coil of a normally open relay 102 which facilitates the distribution of power 102a from power source 104 and power feed line 104a to vehicle circuitry 103. The vehicle circuitry 103 further energizes starter 105 to start the vehicle's engine. As discussed previously, a second possible result generated during the comparison in comparator circuit 300 is an electronic signal 300b indicating an impaired operator whose blood alcohol reading 200a is above, or at, a predetermined blood alcohol concentration level, by example, a threshold level greater than or equal to 0.10 grams of blood per 100 milli-liters. Signal 300b energizes normally open relay 400 and causes distribution of power signal 400a from power source 104 and power feed line 104b to display panel 500. As discussed previously, at display panel 500, the operator is presented with a visual message at message screen 502 to recheck his or her blood alcohol concentration level, and or wait until sober, or get a designated driver whose blood alcohol level will pass the impairedness test for starting the vehicle.

Therefore, while the present invention has been shown and described herein in what is believed to be the most practical and preferred embodiment, it is recognized that departures can be made therefrom within the scope of the invention, which is therefore not to be limited to the details disclosed herein but is to be accorded the full scope of the claims so as to embrace any and all equivalent apparatus.

I claim:

1. A vehicle ignition interlock system apparatus for preventing an alcohol impaired operator from starting a vehicle's engine, said apparatus comprising:
   a non-invasive, blood alcohol concentration tester member, said tester member comprising an electromagnetic energy light source, an incident light collector, a human tissue receptacle, an emanating light collector, a light absorption analyzer, and a blood alcohol concentration generator; and
   electrical and electronic circuitry responsive to a signal generated by said tester member, said electrical and electronic circuitry comprising a blood alcohol concentration comparator for generating a first signal indicative of an operator's non-impaired state for enabling start-up of a vehicle's engine, and for generating a second signal indicative of an operator's impaired state for disabling start-up of a vehicle's engine.

2. A vehicle ignition interlock system apparatus, as described in claim 1, wherein said electrical and electronic circuitry further comprises:
   a message display member;
   a first relay member responsive to a non-impaired state of said operator, said first relay being coupled to a starter member and facilitating starting said vehicle's engine, said first relay being coupled to said message display member for communicating to said operator that starting said vehicle's engine is possible based on non-impaired blood alcohol concentration test result; and
   a second relay member responsive to an impaired state of said operator, said second relay being coupled to said message display member for communicating to said operator that starting said vehicle's engine is not possible based on blood alcohol concentration test results.

3. A vehicle ignition interlock system apparatus, as described in claim 1, wherein said human tissue receptacle comprises:
   a dash mounted unit comprising a port for receiving an operator's finger, said port including a power on/off sensor that facilitates electrically energizing said blood alcohol concentration tester member.

4. A vehicle ignition interlock system apparatus, as described in claim 3, wherein said electrical and electronic circuitry further comprises:
   a message display member;
   a first relay member responsive to a non-impaired state of said operator, said first relay being coupled to a starter member and facilitating starting said vehicle's engine, said first relay being coupled to said message display member for communicating to said operator that starting said vehicle's engine is possible based on non-impaired blood alcohol concentration test result; and
   a second relay member responsive to an impaired state of said operator, said second relay being coupled to said message display member for communicating to said operator that starting said vehicle's engine is not possible based on blood alcohol concentration test results.

5. A vehicle ignition interlock system apparatus, as described in claim 1, wherein said light absorption analyzer comprises:
   light absorption data and corresponding blood alcohol concentration level data.

6. A vehicle ignition interlock system apparatus, as described in claim 5, wherein said human tissue receptacle comprises:
   a dash mounted unit comprising a port for receiving an operator's finger, said port including a power on/off sensor that facilitates electrically energizing said blood alcohol concentration tester member.

7. A vehicle ignition interlock system apparatus, as described in claim 6, wherein said electrical and electronic circuitry further comprises:
   a message display member;
   a first relay member responsive to a non-impaired state of said operator, said first relay being coupled to a starter member and facilitating starting said vehicle's engine, said first relay being coupled to said message display member for communicating to said operator that starting said vehicle's engine is possible based on non-impaired blood alcohol concentration test result; and
   a second relay member responsive to an impaired state of said operator, said second relay being coupled to said message display member for communicating to said operator that starting said vehicle's engine is not possible based on blood alcohol concentration test results.

8. A vehicle ignition interlock system apparatus, as described in claim 1, wherein said electrical and electronic circuitry further comprises:
   a storage member generating an impaired blood alcohol concentration threshold level for being manipulated by said blood alcohol concentration comparator.

9. A vehicle ignition interlock system apparatus, as described in claim 8, wherein said human tissue receptacle comprises:
   a dash mounted unit comprising a port for receiving an operator's finger, said port including a power on/off sensor that facilitates electrically energizing said blood alcohol concentration tester member.

10. A vehicle ignition interlock system apparatus, as described in claim 9, wherein said electrical and electronic circuitry further comprises:
    a message display member;
    a first relay member responsive to a non-impaired state of said operator, said first relay being coupled to a starter member and facilitating starting said vehicle's engine, said first relay being coupled to said message display member for communicating to said operator that starting said vehicle's engine is possible based on non-impaired blood alcohol concentration test result; and
    a second relay member responsive to an impaired state of said operator, said second relay being coupled to said message display member for communicating to said operator that starting said vehicle's engine is not possible based on blood alcohol concentration test results.

11. A vehicle ignition interlock system apparatus for preventing an alcohol impaired operator from starting a vehicle's engine, said apparatus comprising:

a non-invasive, blood alcohol concentration tester member, said tester member comprising an electromagnetic energy light source, and a blood alcohol concentration generator; and electrical and electronic circuitry responsive to a signal generated by said tester member, said electrical and electronic circuitry comprising a blood alcohol concentration comparator for generating a first signal indicative of an operator's non-impaired state for enabling start-up of a vehicle's engine, and for generating a second signal indicative of an operator's impaired state for disabling start-up of a vehicle's engine.

12. A vehicle ignition interlock system apparatus, as described in claim 11, wherein said blood alcohol concentration tester member further comprises:

an incident light collector, a human tissue receptacle, an emanating light collector, and a light absorption analyzer, said human tissue receptacle comprising a dash mounted unit comprising a port for receiving an operator's finger, said port including a power on/off sensor that facilitates electrically energizing said blood alcohol concentration tester member.

13. A vehicle ignition interlock system apparatus, as described in claim 11, wherein said electrical and electronic circuitry further comprises:

a message display member;

a first relay member responsive to a non-impaired state of said operator, said first relay being coupled to a starter member and facilitating starting said vehicle's engine, said first relay being coupled to said message display member for communicating to said operator that starting said vehicle's engine is possible based on non-impaired blood alcohol concentration test result; and a second relay member responsive to an impaired state of said operator, said second relay being coupled to said message display member for communicating to said operator that starting said vehicle's engine is not possible based on blood alcohol concentration test results.

14. A vehicle ignition interlock system apparatus, as described in claim 13, wherein said blood alcohol concentration tester member further comprises:

an incident light collector, a human tissue receptacle, an emanating light collector, and a light absorption analyzer, said human tissue receptacle comprising a dash mounted unit comprising a port for receiving an operator's finger, said port including a power on/off sensor that facilitates electrically energizing said blood alcohol concentration tester member.

15. A method for preventing an alcohol impaired operator from starting a vehicle's engine, said method comprising the steps of:

(a) providing a vehicle ignition interlock system apparatus, said apparatus comprising:

a non-invasive, blood alcohol concentration tester member, said tester member comprising an electromagnetic energy light source, an incident light collector, a human tissue receptacle, an emanating light collector, a light absorption analyzer, and a blood alcohol concentration generator; and electrical and electronic circuitry responsive to a signal generated by said tester member, said electrical and electronic circuitry comprising a blood alcohol concentration comparator for generating a first signal indicative of an operator's non-impaired state for enabling start-up of a vehicle's engine, and for generating a second signal indicative of an operator's impaired state for disabling start-up of a vehicle's engine;

(b) energizing said blood alcohol concentration tester member and positioning an operator's body tissue within said human tissue receptacle and exposing said body tissue to incident light from said electromagnetic energy light source;

(c) absorbing said incident light by said body tissue;

(d) emanating light from said body tissue;

(e) determining quantitative amount of light absorbed by said body tissue;

(f) generating a blood alcohol concentration reading based on said determined quantitative amount of light absorbed by said body tissue;

(g) determining an impaired state based upon said generated blood alcohol concentration reading; and (h) disabling start-up of a vehicle's engine.

16. A method for preventing an alcohol impaired operator from starting a vehicle's engine as described in claim 15; wherein said step (g) alternatively comprises the step of determining a non-impaired state based upon said generated blood alcohol concentration reading, and said step (h) comprises enabling start-up of a vehicle's engine.

17. A method for preventing an alcohol impaired operator from starting a vehicle's engine as described in claim 15; wherein said step (b) comprises said body tissue being an operator's finger, said step (b) further comprises the step of recording optical information about said incident light, and said step (e) comprises determining a difference between said recorded incident light and said emanated light.

18. A method for preventing an alcohol impaired operator from starting a vehicle's engine as described in claim 15; wherein said step (a) includes providing said blood alcohol concentration generator with light absorption data and corresponding blood alcohol concentrations levels relative to predetermined distances of light travel, and said step (f) comprises matching said determined quantitative amount of light absorbed to said provided light absorption data and determining a blood alcohol concentration reading based upon said provided corresponding blood alcohol concentrations levels.

\* \* \* \* \*